United States Patent [19]
Christenson

[11] Patent Number: 5,501,862
[45] Date of Patent: Mar. 26, 1996

[54] ALKYL CARBONATE DERIVATIVES OF SCLAREOL DIOL

[75] Inventor: Philip A. Christenson, Midland Park, N.J.

[73] Assignee: Givaudan-Roure Corporation, Clifton, N.J.

[21] Appl. No.: 173,309

[22] Filed: Dec. 22, 1993

[51] Int. Cl.$^6$ ..................... A23L 1/22
[52] U.S. Cl. ..................... 426/538; 558/260
[58] Field of Search ............. 426/538; 558/260

[56] References Cited

U.S. PATENT DOCUMENTS

| | | | |
|---|---|---|---|
| 2,905,575 | 9/1959 | Giles . | |
| 3,312,226 | 4/1967 | Bauley et al. | 558/260 X |
| 3,818,107 | 6/1974 | Yoller | 99/135 |
| 4,001,438 | 1/1977 | Marmo | 426/96 |
| 4,009,127 | 2/1977 | Ohloff et al. | 549/458 X |
| 4,253,473 | 3/1981 | Marmo | 431/2 |
| 4,538,627 | 9/1985 | Chan | 131/276 |
| 4,538,628 | 9/1985 | Podraza | 131/277 |
| 4,607,118 | 8/1986 | Grubbs | 560/60 |
| 4,678,486 | 9/1986 | Podraza | 549/379 |
| 4,690,157 | 9/1987 | Podraza | 131/276 |
| 4,798,799 | 1/1989 | Farbood et al. | 435/254 |
| 4,872,918 | 10/1989 | Podraza | 131/277 |
| 4,970,163 | 11/1990 | Farbood et al. | 435/255 |
| 5,155,029 | 10/1992 | Farbood et al. | 435/125 |
| 5,212,078 | 5/1993 | Farbood et al. | 435/126 |

FOREIGN PATENT DOCUMENTS 0186502  2/1986  European Pat. Off. .

OTHER PUBLICATIONS

Corbier 1988 Flavors and Fragrances: A World Perspective Proceedings of the 10th Intl Congress of Essential Oils, Fragrances and Flavors. Elsevier Science Publishers Amsterdam pp. 483–494.
Sundararaman & Herz 1977 J Org. Chem 42 (5) 806 Mori & Tamura 1990 Liebigs Ann. Chem 361–368.
Escher & Guersh 1990 Helvetica Acta 73:1935.

Primary Examiner—Carolyn Paden
Attorney, Agent, or Firm—Richard R. Muccino

[57] ABSTRACT

This invention pertains to compounds represented by formula (1):

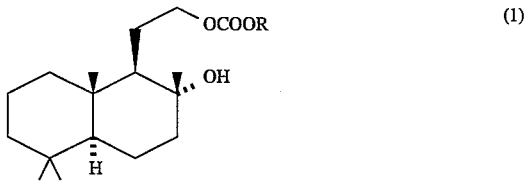

wherein R is selected from the group consisting of branched and unbranched lower-alkyl and lower-cycloalkyl groups having from 1 to 10 carbon atoms. The present invention also provides smoking compositions, and methods for flavoring smoking compositions, which incorporate the novel alkyl sclareol diol carbonates of the invention.

11 Claims, No Drawings

ALKYL CARBONATE DERIVATIVES OF SCLAREOL DIOL

FIELD OF THE INVENTION

This invention relates to novel carbonate derivatives of decahydro-2 -hydroxy-2,5,5,8a-tetramethyl-1-naphthaleneethanol (alkyl carbonate derivatives of sclareol diol) which effectively release a desirable woody amber odor to the mainstream and sidestream smoke of cigarettes. In addition, the novel carbonates are odorless, or nearly odorless, crystalline solids which are stable to storage in cigarettes under ambient conditions. The present invention also provides smoking compositions, and methods for flavoring smoking compositions, which incorporate the novel alkyl carbonate derivatives of sclareol diol of the invention.

BACKGROUND OF THE INVENTION

Flavor additives have long been used to flavor a wide variety of consumer products, particularly tobacco products, foodstuffs, and gums. Flavor additives in such products may be used to mask or attenuate undesirable flavors or odorants, and to enhance existing flavors or odors, or to provide additional flavors or odors not initially present in the consumer product.

In tobacco and tobacco products, flavorants have been added in order to modify or enhance the overall flavor of the product upon use, primarily during smoking. However, the use of many flavorants in tobacco is limited by the volatility or stability of the particular flavorant. Consequently, there is a need for flavorants to be incorporated into tobacco products in such a manner that the flavorant is stable and nonvolatile but then will be released during use. Sylvamber (a Givaudan-Roure trade name for dodecahydro-3a,6,6,9a-tetramethylnaphtho[2,1-B]furan, CAS#6790-58-5) has long been used in fragrances to provide a strong woody amber note. Sylvamber has been reported to be a component of French Tobacco Absolute, B. Corbier, C. Ehret, E. Giraudi and G. Pelerin (Flavors and Fragrances: A World Perspective, Proceedings of the 10th International Congress of Essential Oils, Fragrances and Flavors, B. M. Lawrence, B. D. Mookerjee and B. J. Willis (editors), p. 483–494, Elsevier Science Publishers, Amsterdam, 1988). Sylvamber has also found occasional use as a tobacco flavorant. The utility of Sylvamber, however, is limited by its low odor threshold and its volatility. When used at levels high enough to have a strong impact upon smoking, Sylvamber tends to volatilize from the cigarette into the surrounding pack. In addition, Sylvamber imparts an odor to the unsmoked cigarette which is not acceptable to many smokers.

A principal strategy currently employed to impart flavors and odors to consumer products is admixing the flavorant chemical within a matrix that slows or prevents its release until the product is pyrolyzed, heated, masticated, or wetted. For example, European patent no. 186,502 describes the use of a plastic capsule that releases flavorants when mechanically crushed.

U.S. Pat. No. 4,001,438 describes flavor compositions for use in oral compositions which may be chewing gum compositions, chewable medicinal tablets, chewing tobacco, or toothpaste. The flavor is controllably released from a matrix of solid particles and a suspending agent over an extended period of time under hydrolyric conditions.

U.S. Pat. No. 4,253,473 describes smoking tobacco or substitute smoking tobacco compositions which upon smoking release a flavor from a matrix of solid particles and a suspending agent over an extended period of time.

U.S. Pat. No. 3,818,107 describes a chewing gum containing a flavor release composition comprising flavor groups appended to polymer backbones. The flavor moieties are released from the polymer backbone by hydrolysis during mastication of the chewing gum.

As an alternative method to impart flavors and odors to consumer products, flavoring chemicals have been covalently bound to an auxiliary component to form a higher molecular weight molecule of low volatility. The flavorant is released upon pyrolysis, heating, or solvolysis of the tobacco or food product. For example, U.S. Pat. Nos. 4,701,282 and 4,538,627 describe the use of β-hydroxy-gamma-keto esters as flavorant additives which pyrolyze to release flavorants under cigarette smoking conditions to enhance the flavour of the mainstream smoke and the aroma of sidestream smoke.

U.S. Pat. Nos. 4,690,157 and 4,607,118 describe tobacco compositions containing flavor release additives which pyrolyze in a "retro-aldol" fragmentation reaction into products which enhance the flavor and aroma of cigarette smoke.

U.S. Pat. Nos. 4,578,486 and 4,538,628 describe tobacco compositions which contain dioxane diester flavorant-release additives. When subjected to smoking conditions, the diester additive pyrolyzes to release a volatile alcohol or phenol component which provides flavor-enhancing properties to the mainstream smoke and enhances the aroma of the sidestream smoke.

U.S. Pat. No. 4,872,918 describes a heterocyclic ester which releases tetramethylpyrazine and an olefin upon pyrolysis to improve the flavor and aroma of mainstream and sidestream smoke.

U.S. Pat. No. 2,905,575 describes the use of α-hydroxy-2,5,5,8 a-tetramethyl-1-naphthaleneethanol (sclareol diol) in tobacco to impart a cedar-like aroma to the mainstream smoke. Sclareol diol is odorless when pure and presumably loses a molecule of water during smoking to yield the odorant molecules.

The use of sclareol diol in tobacco, however, presents some drawbacks. Upon smoking, cigarettes containing sclareol diol possess some off-notes not characteristic of Sylvamber. In addition, the effectiveness of sclareol diol declines significantly after one to two months on the cigarette.

Esters of sclareol diol (rather than carbonates) are known compounds. The acetate is not a crystalline solid (W. Herz et. al, *J. Org. Chem.*, 42, 806–813 and K. Mori et. at., *Liebigs Ann. Chem.*, 361–368, 1990), but the epimeric acetate, however, (see structure 14b in G. Ohloff et. al., *Helv. Chim. Acta*, 72, 1935–1947, 1990) is a solid. Precursor molecules which are not solids are generally not useful as flavorants because they are very difficult to obtain pure. In addition, upon pyrolysis, ester derivatives will release the corresponding carboxylic acids which in many cases will have a serious affect upon the flavor.

Accordingly, the present invention provides novel crystalline alkyl carbonate derivatives of sclareol diol which are odorless and stable to storage under ambient conditions but are useful as tobacco flavorants under normal smoking conditions. The present invention also provides smoking compositions, and methods for flavoring smoking compositions, which incorporate the novel alkyl carbonate derivatives of sclareol diol of the invention.

SUMMARY OF THE INVENTION

This invention pertains to compounds represented by formula (1):

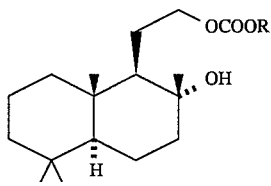

(1)

wherein R is selected from the group consisting of branched and unbranched lower-alkyl and lower-cycloalkyl groups having from 1 to 10 carbon atoms. The present invention also provides smoking compositions, and methods for flavoring smoking compositions, which incorporate the novel alkyl carbonate derivatives of sclareol diol of the invention.

DETAILED DESCRIPTION OF THE INVENTION

The present invention relates to novel carbonate derivatives of decahydro-2-hydroxy-2,5,5,8a-tetramethyl-1-naphthaleneethanol (alkyl carbonate derivatives of sclareol diol) which release a desirable woody amber odor to the mainstream and sidestream smoke of cigarettes. The novel diol carbonates of the present invention are odorless, or nearly odorless, crystalline solids which are stable under normal temperatures and atmospheric conditions, e.g. from about 10° to about 50° C. and from about 20% to about 100% relative humidity. When exposed to elevated temperatures, such as those temperatures developed during the smoking process, the diol carbonates are transformed and odorants and flavorants are released. The diol carbonates of the present invention may be employed to flavor a variety of consumer products such as tobacco products, nontobacco smoking substitutes, medicinal products, and certain foodstuffs.

The alkyl carbonate derivatives of sclareol diol of the present invention may be represented by formula (1):

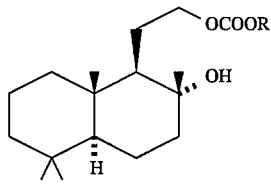

(1)

wherein R is selected from the group consisting of branched and unbranched lower-alkyl and lower-cycloalkyl groups having from 1 to 10 carbon atoms. In a preferred embodiment, R is selected from the group consisting of branched and unbranched lower-alkyl groups having from 1 to 10 carbon atoms. In a more preferred embodiment, R is selected from the group consisting of branched and unbranched lower-alkyl groups having from 1 to 6 carbon atoms. In a most preferred embodiment, R is methyl or ethyl.

The following terms are used throughout the specification and are defined as follows unless otherwise indicated.

The term "carbonate", as used herein refers to an organic compound formed by the addition of carbonic acid (HO—CO—OH, $H_2CO_3$), or a suitable carbonic derivative such as an acid halide, ester, acid halide/ester mixture, or the anhydride ($CO_2$), to a diol.

The terms "flavor", "flavoring", and "flavorant", as used herein, are used interchangeably whenever an organoleptic compound is referred to which is intended to stimulate the sense of taste.

The term "halogen", as used herein, refers to the chemically related elements consisting of fluorine, chlorine, bromine, and iodine.

The term "lower-alkyl", as used herein, means branched- or unbranched-hydrocarbon radicals containing from 1 to 10 carbon atoms, preferably from 1 to 6 carbon atoms. Nonlimiting examples of branched and unbranched lower-alkyl groups having from 1 to 10 carbon atoms are methyl, ethyl, n-propyl, i-propyl, n-butyl, sec-butyl, tert-butyl, n-pentyl, sec-pentyl, tert-pentyl, and the like.

The term "lower-cycloalkyl", as used herein, means cyclic hydrocarbon radicals having from 1 to 10 carbon atoms total, and having from 3 to 6 carbon atoms, preferably from 3 to 5 carbon atoms, in the ring system. Nonlimiting examples of lower-cycloalkyl groups are cyclopropyl, methylcyclopropyl, cyclobutyl, methylcyclobutyl, cyclopentyl, methylcyclopentyl, cyclohexyl, and the like.

The terms "odor", "flagrance", and "smell", as used herein, are used interchangeably whenever a compound is referred to as an organoleptic which is intended to stimulate the sense of smell.

The term "organoleptic", as used herein, refers to compounds of the invention which stimulate the sense of smell or taste, and are thus perceived as having a characteristic odor and/or flavor.

The term "organoleptically effective amount", as used herein, means a level or amount of a novel alkyl sclareol diol carbonate(s) present in a material at which the incorporated compound(s) exhibit(s) a sensory effect.

The terms "tobacco" and "tobacco substitutes", as used herein, are used in the conventional sense and include smokeable as well as nonsmokeable forms in which tobacco is regularly used, e.g., cigarettes, snuff, chewable compositions, etc.

The term "tobacco paper", as used herein, refers to smokeable paper used to contain tobacco, e.g., tobacco rolling paper.

As set out above, the compounds of the invention are odorless crystalline solids which when exposed to elevated temperatures are transformed to odorants or flavorants, or both. The transformation of the novel alkyl carbonate derivatives of sclareol diol to flavorants may be represented as shown below:

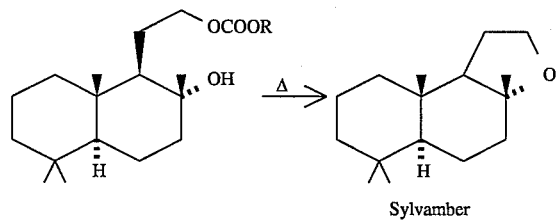

Sylvamber

Thermolysis of the inventive compounds can lead to the formation of products in addition to Sylvamber. Some possible products include sclareol diol and olefinic alcohols and carbonates having the structure shown below:

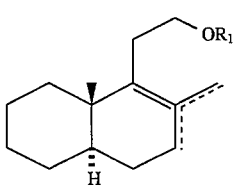

where $R_1$ is hydrogen or COOR, R is as defined above, and the dotted line designates the position(s) of the double bond.

Specific examples of the alkyl carbonate derivatives of sclareol diol of the present invention as well as descriptions of the odor/flavor profile observed during smoking are given below.

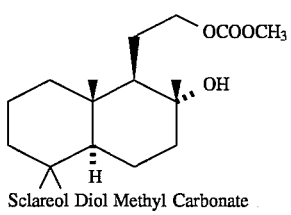

Sclareol Diol Methyl Carbonate

The methyl carbonate imparted a woody cedar-like amber note to the mainstream and sidestream smoke and enhanced the natural tobacco character of the mainstream smoke.

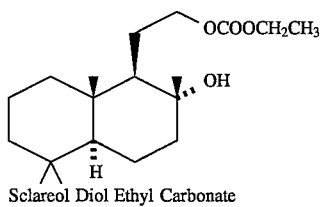

Sclareol Diol Ethyl Carbonate

The ethyl carbonate was similar in character to the methyl carbonate described above but was somewhat stronger in odor and flavor.

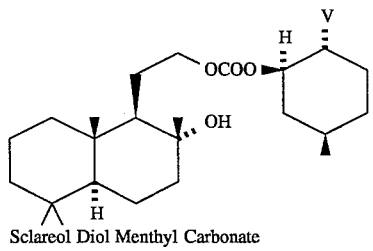

Sclareol Diol Menthyl Carbonate

The menthyl carbonate imparted little if any of the typical Sylvamber note to the mainstream or sidestream smoke.

The alkyl carbonate derivatives of sclareol diol of the invention are stable in cigarettes under prolonged conditions. For example, sclareol diol ethyl carbonate continued to be effective at providing a woody, cedar-like amber note to the mainstream and sidestream smoke on cigarettes after storage under ambient conditions over an 11 month period.

The alkyl carbonate derivatives of sclareol diol of the invention possess organoleptic properties and therefore may be employed in methods for enhancing odor, masking unpleasant odor, or enhancing flavor in foodstuffs and tobacco products. An important property of these alkyl carbonate derivatives of sclareol diol is that the flavorant or odorant is covalently bound as a non-volatile compound and is only released when the tobacco product is ignited and burns. The diol carbonates may be used individually in an organoleptically effective amount to enhance a characteristic flavor or odor of a material. More commonly, however, the diol carbonates are mixed with other flavor or fragrance components in an organoleptically effective amount to provide the desired flavor or odor characteristic.

The amount of alkyl carbonate derivatives of sclareol diol represented by formula (1) required to produce the desired, overall effect is an organoleptically effective amount. An organoleptically effective amount of alkyl carbonate derivatives of sclareol diol present in a material is that amount at which the incorporated diol carbonate exhibits a sensory effect. The exact amount of diol carbonate is a matter of preference and may vary depending upon the particular diol carbonate chosen, the product in which it will be used, and the particular effect desired. In general, the diol carbonates will be present in a product in an amount from about 0.0001% to about 5.0%, preferably from about 0.001% about 1.5%, more preferably from about 0.05% about 0.5%, and most preferably about 0.25%, by weight.

Addition of the alkyl carbonate derivatives of sclareol diol of the present invention either separately or as a mixture onto the media enclosing the tobacco serves to incorporate the odorant/flavorant in the side-stream smoke as the tobacco product burns. This newly formed odorant or flavorant serves to enhance or mask the smoking odors depending upon selection and use levels of the diol carbonates. The compounds of the invention may be incorporated in a foodstuff or tobacco product along with other conventional ingredients such as emulsifiers, carriers, binders, sweeteners, stabilizers, buffers, and solvents.

The compounds of the present invention may be prepared by several methods. In one method, sclareol diol is condensed with chloroformates having the general formula:

Cl—CO—OR in the presence of a proton scavenger in an inert solvent, wherein R is as defined above. In general, chloroformates are known compounds and can be prepared by conventional procedures from other known compounds.

Generally, nitrogen containing proton scavengers such as pyridine, dimethylaminopyridine, N,N-dimethylaniline, and tertiary amines are preferred, but inorganic bases such as sodium carbonate, potassium carbonate, and calcium carbonate may also be used. Pyridine or a mixture of pyridine and dimethylaminopyridine are the most preferred proton scavengers.

A variety of inert solvents (or mixtures of solvents) can be used such as toluene, xylene, heptane, hexane, dichloromethane, dichloroethane, dioxane, t-butyl methyl ether, ethyl ether, dimethoxyethane, or chloroform. Tetrahyrofuran and heptane are preferred solvents. The reaction may be performed in a temperature range from about 0° to about 100° C., and preferably from about 0° to about 50° C.

In another method, the compounds of the present invention can be prepared by condensing sclareol diol with a dicarbonate having the formula

RO—CO—OR in the presence or absence of an inert solvent and in the presence of a catalytic amount of an alkoxide base, wherein R is as defined above. In general, dicarbonates are known compounds and can be prepared by conventional procedures from other known compounds. The alkoxide base may have the general formula MOR, wherein R is as defined above and M is lithium, sodium, or potassium. Regardless of the particular carbonate used, sodium methoxide and ethoxide are the most preferred alkoxides.

Inert solvents, or mixtures of solvents, such as toluene, xylene, dioxane, tetrahydrofuran, dimethoxyethane, dimethyl formamide, diglyme, or heptane may be used. Xylene, toluene, and heptane are the preferred solvents. The reaction may be performed in the temperature range from about 25° to about 150° C., preferably from about 50° C. to about 125° C., and most preferably from about 75° C. to about 100° C.

Throughout this application, various publications have been referenced. The disclosures in these publications are incorporated herein by reference in order to more fully describe the state of the art.

The present invention is further illustrated by the following examples which are presented for purposes of demonstrating, but not limiting, the preparation of the compounds and compositions of this invention.

EXAMPLES

General

All reagents and solvents were commercially available and were used as received. IR spectra were obtained with a Perkin-Elmer 681B Grating Instrument. $^1$H-NMR spectral data reported at 300 MHz were recorded on a Varian Gemini 300. Mass spectra were obtained with a Finnigann INCOS XL GC/MS system. Column chromatography was performed with Merck 60 brand of silica gel. Melting points were determined with a Thomas Hoover Capillary Apparatus and are uncorrected.

Example 1

This Example illustrates the preparation of:

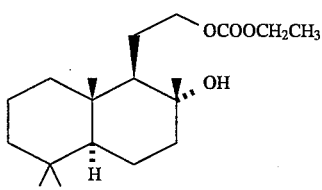

Carbonic acid, ethyl, [1R-(1α,2β,4aβ,8aα)]-
decahydro-2-hydroxy-2,5,5,8a-tetramethyl-1-
naphthaleneethanyl ester Ethyl chloroformate (1.19 g, 0.01 mol) was added dropwise to a cold (0°–5° C.) mixture of [1R-(1α,2β,4 aβ,8aα)] -decahydro-2-hydroxy-2,5,5,8 a-tetramethyl-1-naphthaleneethanol (2.54 g, 0.01 mol), tetrahydrofuran (15 mL), pyridine (1.6 mL) and dimethylaminopyridine (0.122 g, 0.001 mol). After stirring for 1 hour at 0°–5° C., the mixture was allowed to rise to 25° C. Stirring was continued for 16 hours. Ethanol (5 mL) was added. The mixture was stirred for 30 minutes and then added to ice and 2N HCl (20 mL). The mixture was extracted with hexane: ethyl acetate (1:1, 3×20 mL). The organic extracts were washed with 2N HCl (2×15 mL), water (2×10 mL), 5% NaHCO$_3$ (4×15 mL) and brine (15 mL). After drying (Na$_2$SO$_4$), the mixture was concentrated under reduced pressure to provide 3.21 g of a nearly colorless oil. Chromatography (silica gel) provided a colorless oil (3.01 g, 92% yield) which immediately crystallized. Recrystallization (hexane) provided 2.01 g of the title compound as a colorless solid; mp 73°–74° C.

$^1$H-NMR (CDCl$_3$)δ 4.15–4.22 (4H, 2q, overlapping), 1.9–0.9 (15 H, m), 1.30 (3H,t,J=7.1 Hz), 1.16 (3H,s), 0.87 (3H,s), 0.79 (6H,s). IR (CDCl$_3$) 3450, 2950, 1740, 1465 cm$^{-1}$. MS m/e (% abundance) 326 (1), 236 (2), 221 (20), 195 (3), 151 (45), 137 (10), 123 (10), 109 (30), 95 (40), 81 (35), 69 (55), 55 (50), 43 (100), 41 (70).

Example 2

This Example illustrates another method for the preparation of:

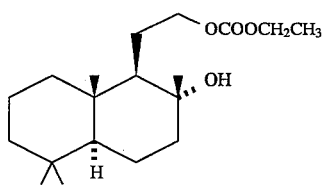

Carbonic acid, ethyl, [1R-(1α,2β,4aβ,8aα)]-
decahydro-2-hydroxy-2,5,5,8a-tetramethyl-1-
naphthaleneethanyl ester A mixture of [1R-(1α,2β,4aβ,8aα)]-decahydro-2-hydroxy-2,5,5,8 a-tetramethyl-1-naphthaleneethanol (2.54 g, 0.01 mol), diethyl carbonate (15 mL) and sodium methoxide (0.054,0.001 mol) was heated at 90°–95° C. for 20 hours. The mixture was cooled to 25° C. and diluted with hexane: ethyl acetate (1:1, 30 mL). The mixture was washed with 1N HCl (10 mL), water (10 mL), 5% NaHCO$_3$ (2×15 mL) and brine. The mixture was dried (Na$_2$SO$_4$) and concentrated under reduced pressure to provide 2.95 g of crude product. Chromatography (silica gel) provided 2.45 g (75% yield) of a colorless solid. Recrystallization gave 1.37 g of a colorless solid identical to the product obtained in Example 1.

Example 3

This Example illustrates the preparation of:

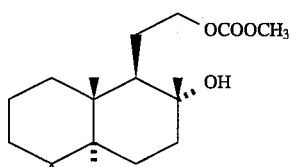

Carbonic acid, methyl, [1R-(1α,2β,4aβ,8aα)]-
decahydro-2-hydroxy-2,5,5,8a-tetramethyl-1-
naphthaleneethanyl ester Methyl chloroformate (1.14 g, 0.011 mol) was reacted with [1R-(1α,2β,4aβ,8aα)] -decahydro-2-hydroxy-2,5,5,8a-tetramethyl-1-naphthaleneethanol (2.54 g, 0.01 mol) in tetrahydrofuran (15 mL) in the presence of pyridine (1.6 mL), and dimethylaminopyridine (0.122 g, 0.001 mol) according to the procedure described in Example 1. Work-up, chromatography and crystallization provided 2.146 g (69% yield) the title compound, mp 46°–49° C.

$^1$H-NMR (CDCl$_3$) δ 4.20 (2H, t, J=7.5 Hz), 3,77 (3H, s), 1.9–0.9 (15H, m), 1.16 (3H, s), 0.87 (3H, s), 0.79 (6H, s). IR (CDCl$_3$) 3460, 2960, 2930, 1745, 1460, 1440 cm$^{-1}$. MS m/e (% abundance) 313 (2), 312 (15), 295 (22), 237 (15), 220 (65), 195 (25), 152 (40), 137 (25), 123 (55), 110 (45), 95 (100), 82 (90), 69 (70), 55 (45), 43 (40).

Example 4

This Example illustrates the preparation of:

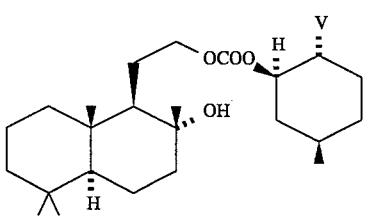

Carbonic acid, [(1R,2S,5R)-2-(1-methylethyl)-5-methyl-cyclohexyl], [1R-(1α,2β,4aβ,8aα)]-decahydro-2-hydroxy-2,5,5,8a-tetramethyl-1-naphthaleneethanyl ester L-Menthyl chloroformate (3.77 g, 0.0173 mol), was reacted with [1 R-(1α,2β,4aβ,8aα)]-decahydro-2-hydroxy-2,5,5,8a-tetramethyl-1-naphthaleneethanol (3.81 g, 0.015 mol) in tetrahydrofuran (25 mL), in the presence of pyridine (2.4 mL and dimethylaminopyridine (0.183 g, 0.0015 mol) according to the procedure described in Example 1. Work-up and crystallization provided 3.682 g (56% yield) of the title compound as colorless crystals, mp 118°–120° C. Recrystallization from hexane provided crystals (2.146 g) of a different shape, mp 107°–108° C. Melting, cooling and remelting gave colorless crystals, mp 118°–120° C.

$^1$H-NMR (CDCl$_3$) 4.55–4.46 (1H, d, t, J=10.9 and 4.4 Hz), 4.21 (2H, t, J=7.3 Hz) 2.1–0.8 (24H, m), 1.17 (3H, s), 0.93–0.89 (6H, 2d), 0.87 (3H,s), 0.80–0.78 (3H, d) 0.79 (6H,s). IR (CDCl$_3$) 3480, 2970, 1835, 1455 cm$^{-1}$. MS m/e (% abundance), 436 (3), 419 (20), 298 (25), 281 (25) 237 (12), 220 (60), 195 (40), 151 (50), 123 (40), 109 (40), 96 (55), 82 (100), 69 (55), 57 (50), 43 (50).

Example 5

This Example illustrates the preparation of a smoking composition comprising tobacco in combination with an organically effective amount of the ethyl carbonate compound described in Example 1.

Carbonic acid, ethyl, [1R-(1α,2β,4aβ, 8aα)]-decahydro-2-hydroxy-2,5,5,8 a-tetramethyl-1-naphthaleneethanyl ester, from Example 1, was incorporated into standard brand 100% flue-cured filter cigarettes at a level of 25 ppm. The cigarettes were smoked and the flavor character compared to the flavor of the untreated standard brand cigarettes. The cigarettes containing the ethyl carbonate compound described in Example 1 were found to impart a woody, cedar-like amber note to both the mainstream and sidestream smoke and to enhance the natural tobacco character.

Example 6

This Example illustrates another preparation of a smoking composition comprising tobacco in combination with an organically effective amount of the methyl carbonate compound described in Example 3.

Carbonic acid, methyl, [1R-(1α,2β,4aβ, 8aα)]-decahydro-2-hydroxy- 2,5,5,8a-tetramethyl-1-naphthaleneethanyl ester, from Example 3, was incorporated into standard brand 100% flue-cured filter cigarettes at a level of 25 ppm. Evaluation as described in Example 5 revealed that the cigarettes containing the compound from Example 3 imparted to the mainstream and sidestream smoke a flavor very similar in character to that observed in Example 5, but somewhat less intense.

Example 7

This Example illustrates the storage stability of a smoking composition comprising tobacco in combination with an organically effective amount of the ethyl carbonate compound described in Example 1.

Carbonic acid, methyl, [1R-(1α,2β,4aβ, 8aα)]-decahydro-2-hydroxy- 2,5,5,8a-tetramethyl-1-naphthaleneethanyl ester, from Example 1 was incorporated into standard brand 100% flue-cured filter cigarettes at a level of 20 ppm. The cigarettes were stored under ambient conditions in a sealed jar. The cigarettes were smoked at regular intervals over an eleven month period. During that time period, the cigarettes continued to display a strong woody, cedar-like amber note in the mainstream and sidestream smoke.

While we have represented a number of embodiments of this invention, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

I claim:
1. A compound represented by formula (1):

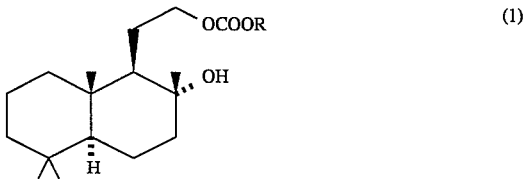

wherein R is selected from the group consisting of branched and unbranched lower-alkyl and lower-cycloalkyl groups having from 1 to 10 carbon atoms.

2. The compound according to claim 1, wherein R is selected from the group consisting of branched and unbranched lower-alkyl groups having from 1 to 10 carbon atoms.

3. The compound according to claim 2, wherein R is selected from the group consisting of branched and unbranched lower-alkyl groups having from 1 to 6 carbon atoms.

4. The compound according to claim 3, wherein R is methyl or ethyl.

5. A composition suitable for human consumption which comprises a consumable material in combination with an organoleptically effective amount of a compound represented by formula (1):

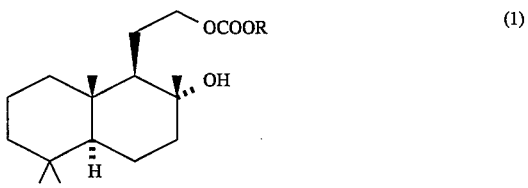

wherein R is selected from the group consisting of branched and unbranched lower-alkyl and lower-cycloalkyl groups having from 1 to 10 carbon atoms.

6. The composition according to claim 5, wherein R is selected from the group consisting of branched and unbranched lower-alkyl groups having from 1 to 10 carbon atoms.

7. The composition according to claim 6, wherein R is selected from the group consisting of branched and unbranched lower-alkyl groups having from 1 to 6 carbon atoms.

8. The composition according to claim 7, wherein R is methyl or ethyl.

9. The composition according to claim 5, wherein the concentration of the compound represented by formula (1) is from about 0.0001% to about 5.0%, by weight.

10. The composition according to claim 9, wherein the concentration of the compound represented by formula (1) is from about 0.001% to about 1.5%, by weight.

11. The composition according to claim 5, wherein the consumable material is a foodstuff.

* * * * *